United States Patent [19]

Temple John E.

[11] Patent Number: 4,850,986
[45] Date of Patent: Jul. 25, 1989

[54] INCONTINENCE DEVICE

[75] Inventor: Temple John E., Chelsea, Mich.

[73] Assignee: Midwest Medical Co., Chelsea, Mich.

[21] Appl. No.: 98,073

[22] Filed: Sep. 18, 1987

[51] Int. Cl.$^4$ ................................................ A61F 5/44
[52] U.S. Cl. .................................... 604/355; 604/349; 604/332
[58] Field of Search ......................... 604/355, 349, 332

[56] References Cited

U.S. PATENT DOCUMENTS

| | | | |
|---|---|---|---|
| 2,448,938 | 4/1948 | Wayne | 128/285 |
| 2,548,149 | 4/1951 | Fowler | 604/355 |
| 2,564,773 | 8/1951 | Wade | 128/275 |
| 3,522,807 | 8/1970 | Millenbach | 128/283 |
| 3,523,534 | 8/1970 | Nolan | 128/283 |
| 3,804,093 | 4/1974 | Fell | 604/355 |
| 4,253,460 | 3/1981 | Chen et al. | 128/283 |
| 4,445,898 | 5/1984 | Jensen | 604/337 |
| 4,496,356 | 1/1985 | Lognion | 604/328 |
| 4,650,817 | 3/1987 | Allen, Jr. et al. | 523/105 |

FOREIGN PATENT DOCUMENTS 7703562 10/1978 Netherlands ..................... 604/355
113453 4/1977 Switzerland ..................... 604/328

OTHER PUBLICATIONS

Hollister Fecal Incontinence Collector Brochure, 7 pages, Copyright 1986, by Hollister Inc., 2000 Hollister Drive, Libertyville, Illinois 60048.

Primary Examiner—Larry Jones
Attorney, Agent, or Firm—James M. Deimen

[57] ABSTRACT

An incontinence device comprising a generally tubular soft latex shape open at both ends. The upper end is smoothly curved and tapered inward to the opening with the latex of minimal thickness and coated on the outside adjacent the opening with a suitable adhesive for contact with the skin about the anal opening. The lower end is partially folded and clipped to permit the device to be affixed with an applicator specifically shaped for the purpose and inserted within the device. The shape and material of the device permits the device to fully stretch and shrink with the anal opening while remaining adhesively affixed to the skin.

18 Claims, 5 Drawing Sheets

INCONTINENCE DEVICE

BACKGROUND OF THE INVENTION

The field of the invention pertains to medical appliances and, in particular, to devices that can be attached to the exterior skin of a person about or in an opening with the purpose of accepting and containing any solid or liquid material flowing from the opening. Such devices require a means of attachment that does not damage the skin but is reasonably secure.

Lognion, U.S. Pat. No. 4,496,356, discloses an anal excretion collecting rectal catheter that is insertable beneath the sphincter muscles about the opening. The Lognion device comprises a collecting tube open at one end with a resilient ring that fits within the rectal opening.

Wade, U.S. Pat. No. 2,564,773, discloses a therapeutic agent comprising a thimble and latex bag insertable into a bodily opening for the collection of fluids. The bag folds within the thimble before use and may be attached to the thimble with an adhesive. The thimble includes an opening for the admission of fluids and is directly insertable into the bodily opening.

Wayne, U.S. Pat. No. 2,448,938 and Swiss Pat. No. 113 453 each disclose a sanitary protective appliance of similar structure to receive bodily fluids and semi-solids from infections and incisions. The appliances comprise soft thin rubber tubes of accordion like shape with an opening of relatively large diameter. On the inside surface adjacent the opening is an adhesive ring to enable the device to be adhesively attached to the skin about the body opening from which there is a discharge.

Chen et al., U.S. Pat. No. 4,253,460 and Allen, Jr. et al., U.S. Pat. No. 4,650,817 both disclose adhesives suitable for attaching appliances such as ostomy devices to the skin about a body opening. Such adhesives must be secure, reasonably fluid tight but nevertheless easy to remove without damage to the skin.

U.S. Pat. No. 3,522,807 discloses an incontinence bag that has a pleated arrangement about the anus to expand and contract with the opening and closing of the anus. The overlapping leaves of the pleats do not provide for complete adhesive attachment to the skin thus permitting leakage and providing a difficult attachment.

U.S. Pat. No. 4,445,898 discloses a foam backed skin barrier attachment and incontinence bag. The skin barrier is disclosed as soft, pliable, stretchable and contractable foam backed plastic 0.080 to 0.400 inches thick. Plastic backed by foam has limited stretchability if less than 25% which limits the expandability of the anal hole in the skin barrier to an amount less than needed for many patients. In such cases, the anus can not open sufficiently thereby causing severe pain or the adhesive fails and the bag detaches and leaks.

Devices insertable within body openings have been found to cause permanent damage to the sphincter muscles after prolonged use. With a view toward overcoming and avoiding damage to the sphincter muscles of the anal opening but nevertheless providing a secure receptacle for body waste that does not damage the skin surrounding the anus, is sufficiently elastic (an elastic limit of about 200% or more) to accomodate the full opening of the anus and is easy to install the following described incontinence device has been developed.

SUMMARY OF THE INVENTION

The incontinence device comprises a generally tubular soft latex shape, tube or bag open at both ends but having a clip to retain the lower end partially folded up and closed. The upper end of the device is curved and tapered inward to the opening with the latex of minimal thickness, preferably 0.003 to 0.006 inches, and coated on the outside with a suitable adhesive for contact with the skin about the anal opening. The latex is purposefully made as thin as possible to enable the latex to offer little or no resistance to stretching with the skin as the anus is fully opened and closed by the sphincter muscles. Soft latex of the above thickness has a better than 400% elastic limit.

A specifically shaped applicator is provided to enable a nurse or physician to easily apply the adhesive to the device and to conveniently and securely attach the adhesive and latex about the upper opening to the skin about the anus. The applicator fits within the tube and is removed through the lower end of the tube. The clipped lower end also permits the tube to be periodically opened to permit gases accumulated therein to be expelled, or fecal matter to be removed and the bag to remain on patient.

DESCRIPTION OF THE PREFERRED EMBODIMENTS

Figure 1:
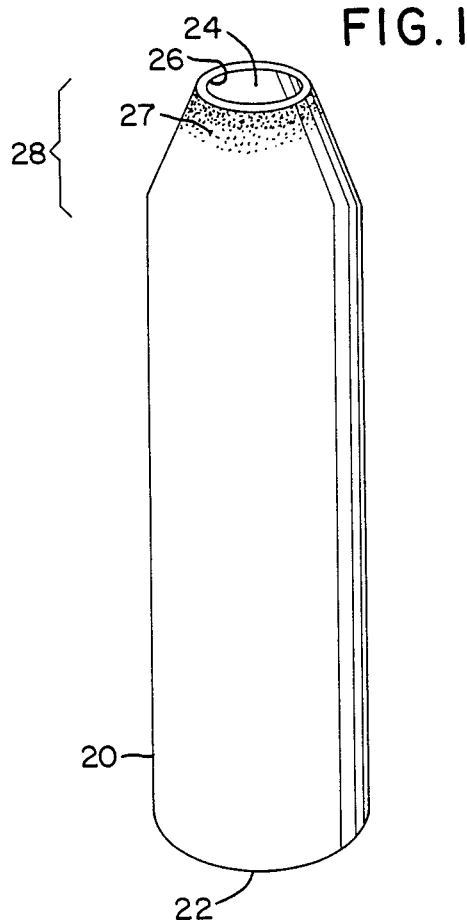
FIG. 1 is a perspective view of the device.
Figure 3:
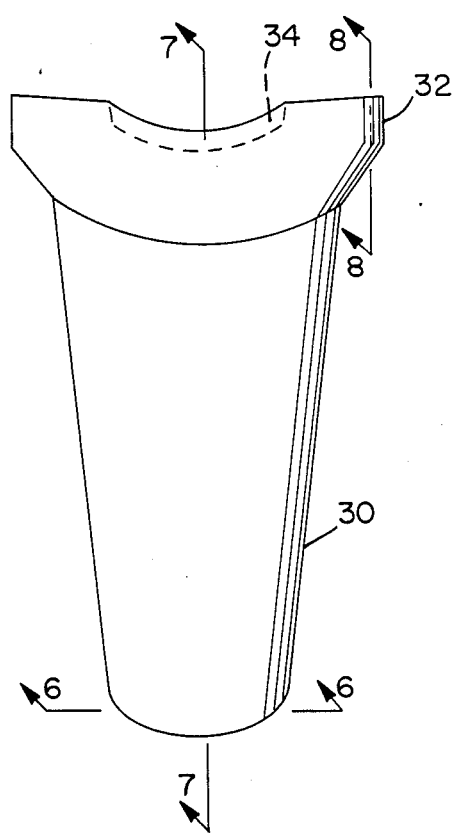
FIG. 3 is a perspective view of the applicator.
Figure 2:
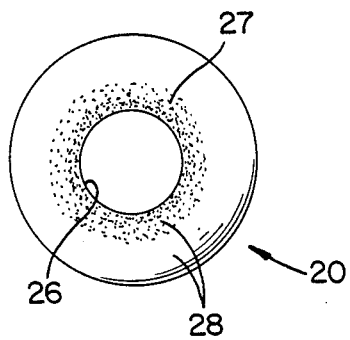
FIG. 2 is an upper end view of the device.
Figure 4:
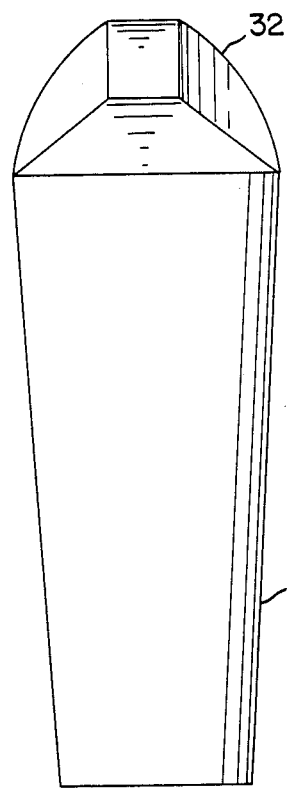
FIG. 4 is an end view of the applicator.
Figure 5:
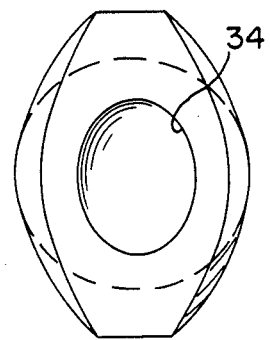
FIG. 5 is a top view of the applicator.
Figure 6:
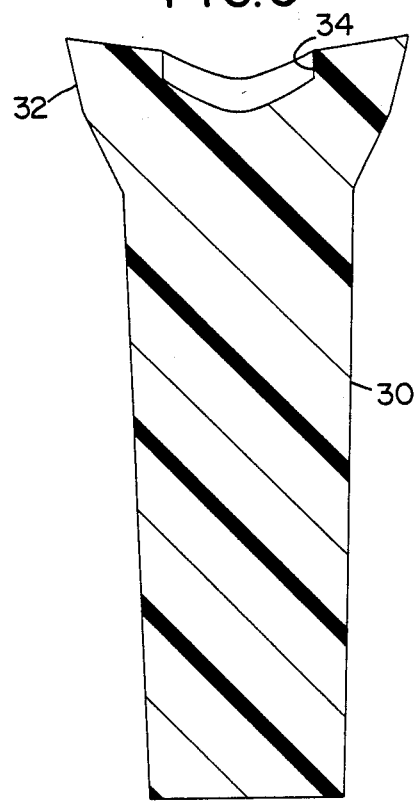
FIG. 6 is a cross-section of the applicator taken along the line 6—6 of FIG. 5.
Figure 7:
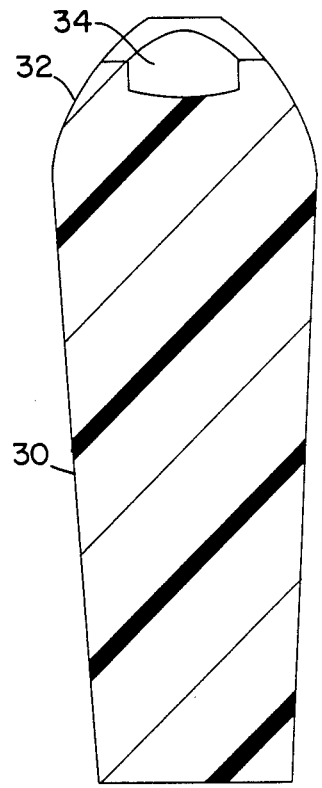
FIG. 7 is a cross-section of the applicator taken along the line 7—7 of FIG. 3.
Figure 8:
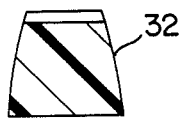
FIG. 8 is a cross-section of the applicator taken along the line 8—8 of FIG. 3.

Illustrated in FIGS. 1 and 2 is a generally tubular shape 20 formed of soft latex or a similar material that is liquid impermeable, very flexible and soft to the skin. The lower end 22 is open. As illustrated below the lower end may be closed by folding over and retaining with a plastic closure clip (not shown). The device is suitably about 18 inches long and 3 inches in diameter. With the exception of the upper end 24 a wall thickness of about 0.010 to 0.0020 inches is suitable.

The upper end 24 includes an opening 26 of about one and one-quarter inches in diameter surrounded by an upper curved generally conical portion 28 extending down to the tubular shape 20. The curved upper portion 28 is made specifically very thin for maximum elasticity and flexibility and adjacent the opening 26 is coated on the outside 27 just prior to use with an adhesive suitable for secure attachment to the skin.

Since the human skin about the anal opening stretches and contracts a substantial amount with opening and closing of the anal sphincter muscles, the conical portion 28 must also stretch and contract with minimal resistance and maximum flexibility to prevent chafing of the skin and failure of the adhesive attachment. A thickness of 0.003 to 0.006 inches for soft latex has been found preferable with a two part adhesive comprising polyolmethylsiloxane in trichlorotriflouroethane. Thicknesses of about 0.015 inches for the latex adjacent the upper opening have been found too inflexible for satisfactory use although a thickness of less than 0.010 inches is serviceable. The thinned latex has been found far superior to plastics by providing elasticity on the order of 400%, or more.

The inside of the device is preferably coated with a powder to prevent the sticking of stools to the inside of the latex tube. Cornstarch, baby powder or medical grade silicone lubricant are suitable materials.

Figure 9:
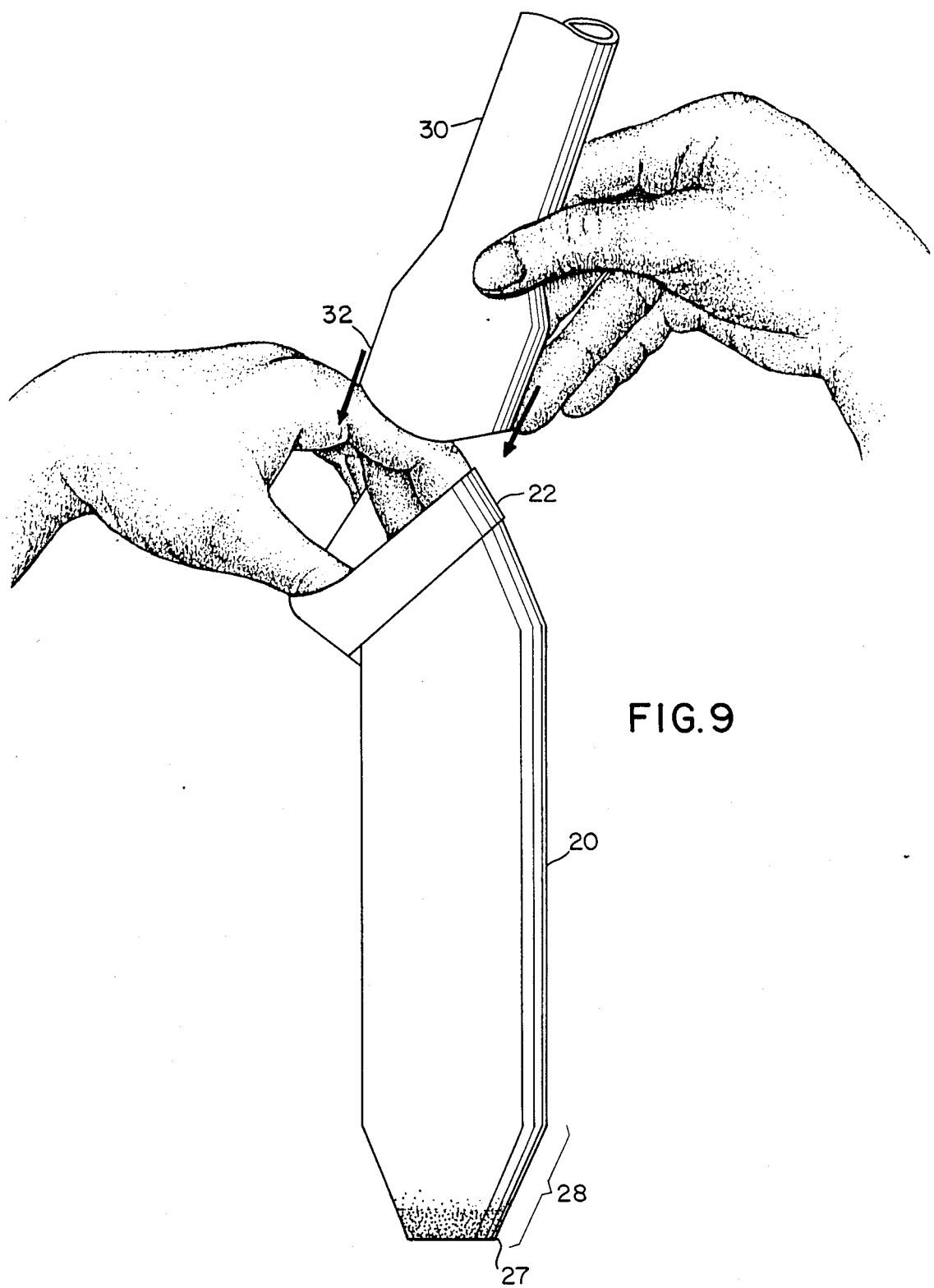
FIG. 9 illustrates insertion of the applicator into the device.

Illustrated in FIGS. 3 through 8 is an applicator comprising a handle portion 30 and shaped top 32. As shown the top 32 is generally saddle shaped with a depressed oval center 34. The saddle shape 32 is specifically to fit the skin and muscle structure about the human male or female anus. The saddle shape 32 is sized to fit within the conical portion 28 of the device. More particularly, the conical portion 28 is stretched over the applicator saddle shape 32 after insertion of the applicator from the open lower end 22 as shown in FIG. 9.

Figure 10:
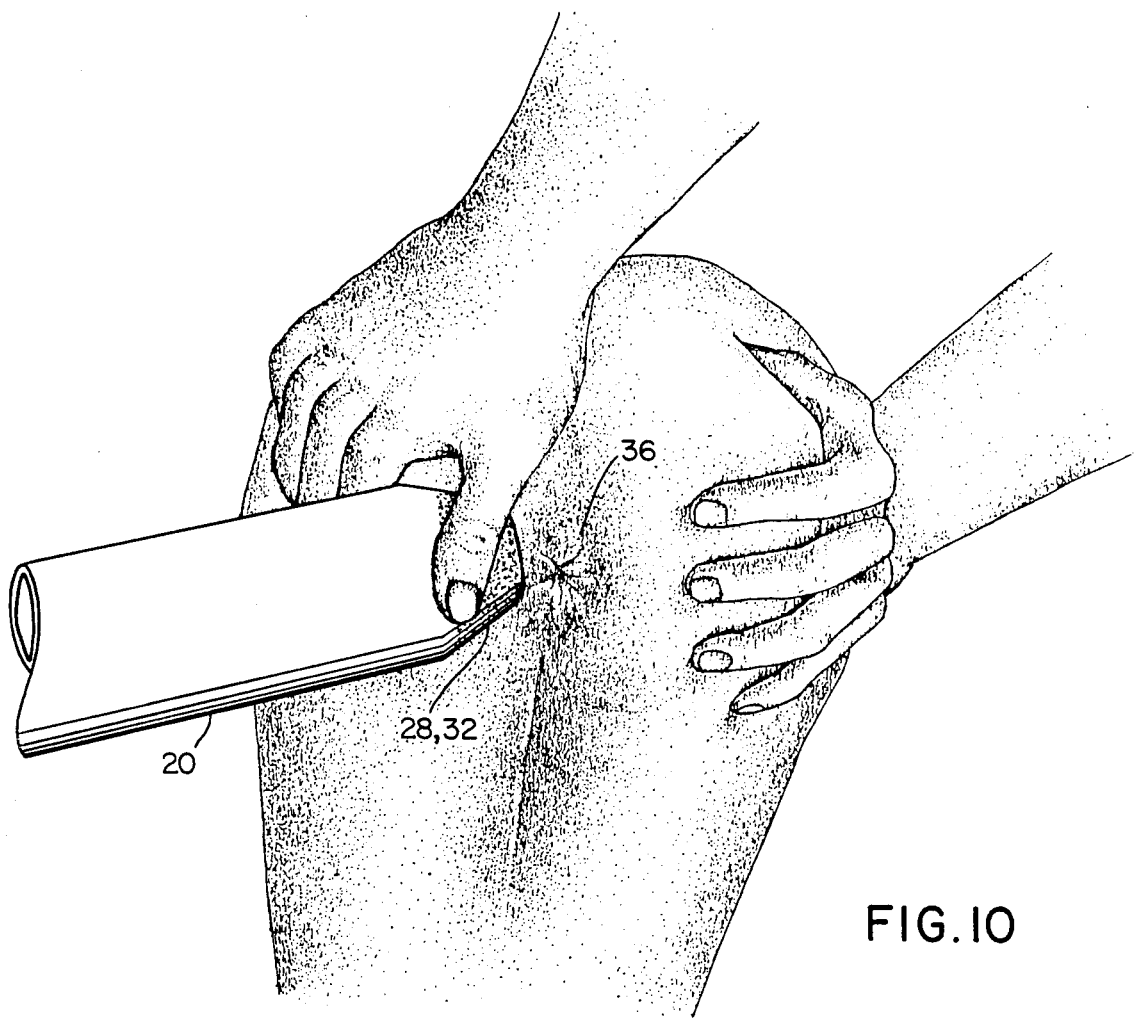
FIG. 10 illustrates attachment of the device.
Figure 11:
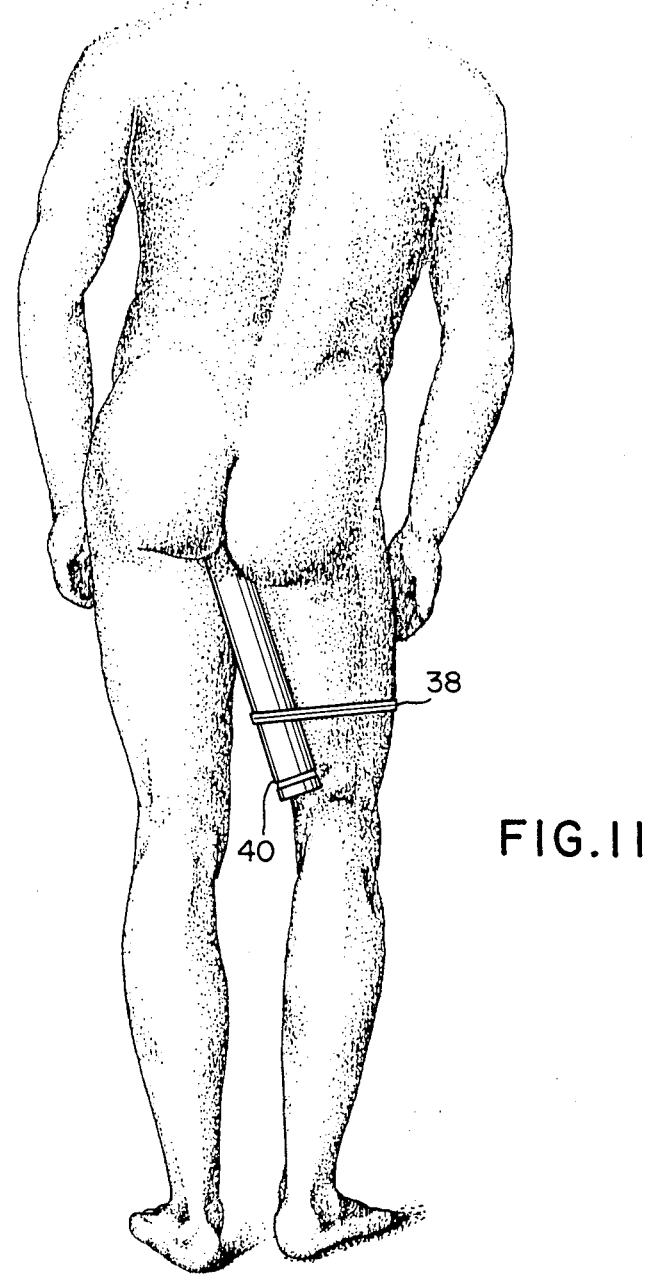
FIG. 11 illustrates the device in place.

As best shown in FIG. 10 the device 20 with the applicator held thereinside and the conical portion 28 stretched smoothly over the saddle shape 32 is coated with adhesive and applied about the anus 36. In place as shown in FIG. 11 the device may be lightly taped at 38 to the thigh and folded and clipped at 40.

What is claimed is:

1. An incontinence device comprising a thin-walled substantially tubular shape, an opening in the upper end of the tubular shape, said opening of substantially less diameter than the tubular shape, said tubular shape tapered to said opening and said taper of the tubular shape adapted to flexibly conform to the skin covering the sphincter muscles about a natural bodily orifice,
    an adhesive applied to the outside of said taper about said opening, and
    said taper about said opening sufficiently thin, soft, flexible and elastic with an elongation substantially equal or greater than the skin covering the sphincter muscles so as to expand and contract with the skin about the natural bodily orifice without hindrance to the expansion and contraction of the skin and sphincter muscles.

2. The incontinence device of claim 1 wherein the interior surface of the tubular shape is coated with a non-stick material.

3. The incontinence device of claim 1 wherein the thickness of the taper about said opening is less than 0.010 inches and is made of soft latex.

4. The incontinence device of claim 1 wherein the tubular shape is constructed of soft latex, said latex being tapered in thickness toward the upper end opening to provide an elastic limit of at least 200%.

5. The incontinence device of claim 1 including an opening in the lower end of the tubular shape, means to conveniently close and open the lower opening and means to attach the device to a thigh.

6. The incontinence device of claim 1 wherein the device is curvedly tapered about the opening in the upper end.

7. The incontinence device of claim 1 wherein said adhesive is a sprayed on coating applied just prior to attachment to the skin.

8. An incontinence device comprising a thin-walled oblong soft latex tube, an opening in the upper end of the tube, said tube being curvedly tapered to the opening and said curved taper of the tube adapted to flexibly conform to the human skin covering the sphincter muscles about the anus,
    an adhesive applied to the outside surface of the tube about the opening,
    a non-stick coating on the inside surface of the tube, and
    said tube taper thinned to a wall thickness about the opening providing a flexibility, elongation and elasticity at least equal to or greater than the flexibility, elongation and elasticity of human skin about the anus whereby upon attachment of the taper about the anus the human skin so attached can expand and contract without hindrance.

9. The incontinence device of claim 8 wherein the bulk of the tube is about 0.012 inches in thickness and the tube is tapered to a thickness of about 0.006 inches about the upper end opening.

10. The incontinence device of claim 9 including an opening in the lower end of the tube, means to conveniently close and open the lower opening and means to attach the device to a thigh.

11. The incontinence device of claim 8 wherein the elastic limit of the soft latex about the upper opening is substantially 400%.

12. The incontinence device of claim 8 wherein said adhesive is a sprayed on coating applied just prior to attachment to the human skin about the anus.

13. An incontinence device applicator for an incontinence device having a soft elastic tapered upper end, the applicator comprising a handle, a saddle shaped portion appended to one end of the handle, and an oval depressed center in the saddle shaped portion, said saddle shaped portion sized to fit within the tapered upper end of such an incontinence device.

14. The method of attaching an incontinence device about the human anus comprising stretching the tapered upper end of an incontinence device over a saddle shaped applicator end, applying an adhesive surface to the outside of the tapered end, and while holding the applicator from within the incontinence device applying the saddle shaped end and tapered end of the incontinence device against the skin about the anus.

15. The method of attaching an incontinence device about the human anus comprising stretching the upper end of an incontinence device over a specifically shaped applicator end and while holding the applicator within the incontinence device applying the applicator end and upper end of the device against the skin about the anus.

16. An incontinence device and an applicator therefor in combination comprising a thin walled substantially tubular shape of soft, flexible elastic material, a hole in the upper end of the device, said hole surrounded by a soft elastic tapered upper end of the device, an applicator, said applicator comprising a handle and a saddle shaped portion appended to the handle, said saddle shaped portion sized to fit within the tapered upper end of the device.

17. The incontinence device and applicator of claim 16 wherein the applicator upon insertion in the device causes the soft elastic tapered upper end of the device to substantially conform to the saddle shaped portion of the applicator.

18. An incontinence device comprising a thin-walled hollow membranous shape having an upper portion, an opening in the upper portion of the membranous shape, said upper portion surrounding the opening sufficiently thin to conform to the skin covering the sphincter muscles about the human anus and said upper portion surrounding the opening exhibiting sufficient elongation that upon tight attachment to the skin about the anus to permit full expansion and contraction of the anus without hindrance or detachment of the device.

* * * * *